(12) United States Patent
Gilmartin et al.

(10) Patent No.: US 11,172,876 B2
(45) Date of Patent: Nov. 16, 2021

(54) ACOUSTIC SENSOR PLATFORM METHOD AND APPARATUS FOR PAIN MITIGATION, APNEA DETECTION, ASPIRATION DETECTION AND PATIENT COMMUNICATION IN ANESTHESIA PATIENTS

(71) Applicants: Charles Gilmartin, San Anselmo, CA (US); Rob K. Rao, Moraga, CA (US)

(72) Inventors: Charles Gilmartin, San Anselmo, CA (US); Rob K. Rao, Moraga, CA (US)

( * ) Notice: Subject to any disclaimer, the term of this patent is extended or adjusted under 35 U.S.C. 154(b) by 223 days.

(21) Appl. No.: 16/351,666

(22) Filed: Mar. 13, 2019

(65) Prior Publication Data

US 2019/0282160 A1    Sep. 19, 2019

Related U.S. Application Data

(60) Provisional application No. 62/642,079, filed on Mar. 13, 2018.

(51) Int. Cl.
*A61B 5/00* (2006.01)
*A61B 5/08* (2006.01)
(Continued)

(52) U.S. Cl.
CPC .............. *A61B 5/4821* (2013.01); *A61B 5/01* (2013.01); *A61B 5/0803* (2013.01); *A61B 5/0816* (2013.01); *A61B 5/0826* (2013.01); *A61B 5/0836* (2013.01); *A61B 5/14539* (2013.01); *A61B 5/4803* (2013.01); *A61B 5/6803* (2013.01); *A61B 5/7203* (2013.01);
(Continued)

(58) Field of Classification Search
CPC ... A61B 5/4821; A61B 5/4803; A61B 5/6803; A61B 5/7203; A61B 5/0816; A61B 5/0826; A61B 5/746; A61B 5/0836; A61B 5/14539; A61B 5/01; A61B 5/0803; A61B 5/742; A61B 2505/05
See application file for complete search history.

(56) References Cited

U.S. PATENT DOCUMENTS

2015/0157817 A1* 6/2015 Steiner, III ............ A61M 16/06
                                                        128/206.22
2019/0224434 A1* 7/2019 Silver .................... A61H 31/00

OTHER PUBLICATIONS

Vincent J. Kopp, M.D.; Audrey Shafer, M.D. Anesthesiologists and Perioperative Communication, Anesthesiology 8 2000, vol. 93, 548-555.

(Continued)

*Primary Examiner* — Rex R Holmes
(74) *Attorney, Agent, or Firm* — Blynn L. Shideler; Krisanne Shideler; BLK Law Group

(57) ABSTRACT

An acoustic sensor platform based method and apparatus provides for improved pain mitigation, apnea detection, aspiration detection and patient communication in anesthesia patients. The platform includes an acoustic sensor configured to be coupled to one of a nasal cannula or face mask of the anesthesia patient; a processer coupled to the acoustic sensor and configured to i) Detect patient speech and isolate and amplify the patient speech, and ii) Detect at least one of a breathing rate of the patient or aspiration of the patient; and an audio visual display coupled to the processor and providing an audio and/or visual display of the isolated and amplified speech of the patient, and displaying results for at least one of a breathing rate of the patient or aspiration of the patient.

19 Claims, 1 Drawing Sheet

(51) Int. Cl.
    *A61B 5/083*     (2006.01)
    *A61B 5/145*     (2006.01)
    *A61B 5/01*     (2006.01)

(52) U.S. Cl.
    CPC .............. *A61B 5/742* (2013.01); *A61B 5/746* (2013.01); *A61B 2505/05* (2013.01)

(56) References Cited

OTHER PUBLICATIONS

John Kyle Bohman, M.D., Aspiration during Monitored Anesthesia Care, Anesthesiology 2 2015, vol. 122, 471-472.

Savilampi, J, Ahlstrand, R, Magnuson, A, Geijer, H, Wattwil, M. Aspiration induced by remifentanil: A double-blind, randomized, crossover study in healthy volunteers, Anesthesiology. (2014). 121 52-8.

Soto, Roy G. MD; Fu, Eugene S. MD; Vila, Hector Jr. MD; Miguel, Rafael V. MD, Capnography Accurately Detects Apnea During Monitored Anesthesia Care, Anesthesia & Analgesia: Aug. 2004—vol. 99—Issue 2—p. 379-382.

\* cited by examiner

ACOUSTIC SENSOR PLATFORM METHOD AND APPARATUS FOR PAIN MITIGATION, APNEA DETECTION, ASPIRATION DETECTION AND PATIENT COMMUNICATION IN ANESTHESIA PATIENTS

RELATED APPLICATIONS

This application claims priority to U.S. Patent Application Ser. No. 62/642,079 filed Mar. 13, 2018 titled "Method and Apparatus for Pain Mitigation, Apnea Detection, Aspiration Detection and Patient Communication in Anesthesia Patients" which is incorporated herein by reference in its entirety.

BACKGROUND INFORMATION

1. Field of the Invention

The present invention relates to improving anesthesia procedures, and more specifically to an acoustic sensor platform method and an apparatus for pain mitigation, apnea detection, aspiration detection and patient communication in anesthesia patients.

2. Background Information

Not all surgeries have to be done with general anesthesia; i.e., the type that renders the patient unconscious. Sometimes, light sedation (usually used to supplement local numbing injections) is enough to keep the patient comfortable. Possible options for sedation are light, moderate, or deep—depending on the situation. The continuum of consciousness, as relates to anesthesia, proceeds as follows: awake (no sedation); lightly sedated; moderately sedated; deeply sedated; unconscious (under general anesthesia). Further it is not always possible to predict the level of sedation that will be needed by a specific patient for a specific procedure.

Monitored anesthesia care (MAC) means that an anesthesiologist (or nurse anesthetist, anesthesia resident, anesthesiology assistant) is present and responsible for the sedation, care, and monitoring of the patient during the procedure. Any level of sedation can be a MAC anesthetic, and for a MAC anesthetic, the anesthesiologist will assess the patient preoperatively, monitor and medicate intraoperatively, and direct the recovery postoperatively.

An important aspect of MAC is communication between the patient and the anesthesiologist. As discussed in *Anesthesiologists and Perioperative Communication*, Vincent J. Kopp, M.D.; Audrey Shafer, M.D. Anesthesiology 8 2000, Vol. 93, 548-555, communication between the patient and the anesthesiologist is helpful in preoperative, intraoperative, and postoperative stages. Intraoperative communication with patients can greatly assist the effective monitoring and medication stratagems for the anesthesiologist and can mitigate patient pain and improve patient outcomes.

Regurgitation and aspiration during anesthesia is a long recognized complication that was first recognized as a cause of an anesthetic-related death in 1848. Aspiration is inhalation of material into the airway and it has been linked with a range of detrimental clinical outcomes. See *Aspiration during Monitored Anesthesia Care*, John Kyle Bohman, M.D., Anesthesiology 2 2015, Vol. 122, 471-472; *Aspiration induced by remifentanil: A double-blind, randomized, crossover study in healthy volunteers*, Savilampi, J, Ahlstrand, R, Magnuson, A, Geijer, H, Wattwil, M. ANESTHESIOLOGY. (2014). 121 52-8. Although some in the field have differentiated between pharyngeal-to-pulmonary aspiration (either oropharyngeal or nasopharyngeal) and gastric-to-pulmonary aspiration regarding patient outcomes, it is agreed that prompt detection of all aspiration is an important aspect of MAC for improving patient outcomes.

Hypoventilation, apnea, and airway obstruction (combined herein under apnea) are also common complications encountered during procedural sedation. Pulse oximetry, routinely used during monitored anesthesia care (MAC)/ sedation, is a reliable estimate of oxygenation; however, detection of apnea or airway obstruction, as evidenced by a decline in arterial oxygen saturation ($SpO_2$), can be delayed, especially when patients are breathing supplemental oxygen. Electrical impedance respiratory rate monitoring is also a well-established technique for monitoring apneic episodes, but it can be technically difficult, depending on the surgical site. Also, chest wall movement can occur with airway obstruction, which is interpreted by an impedance monitor as "breathing". Capnography, the monitoring of the concentration or partial pressure of carbon dioxide ($CO2$) in the respiratory gases, has been used to monitor apnea and airway obstruction in MAC/sedated patients as discussed in *Capnography Accurately Detects Apnea During Monitored Anesthesia Care*, Soto, Roy G. MD; Fu, Eugene S. MD; Vila, Hector Jr. MD; Miguel, Rafael V. MD, Anesthesia & Analgesia: August 2004—Volume 99—Issue 2—p 379-382.

With the desire for fast turn over times between the end of a surgery procedure and the start of the next procedure, many patients are being delivered to the recovery room with a level of anesthesia that will only allow them to be aroused with painful stimulation, which unfortunately increases the likelihood of undetected micro-aspiration. This in combination with lack of an anesthesia provider constantly at the patient's side in the recovery room, makes a monitoring/ detection device critical for the reduction of morbidity and mortality.

There remains a need in the art for improving anesthesia procedures for pain mitigation, apnea detection, aspiration detection and patient communication in anesthesia patients and to provide a monitoring/detection device that is cost effective and can be critical for the reduction of morbidity and mortality.

SUMMARY OF THE INVENTION

One aspect of this invention is directed to an acoustic sensor based method and apparatus for pain mitigation, apnea detection, aspiration detection and patient communication in anesthesia patients.

One aspect of this invention may be defined as providing an acoustic sensor platform for anesthesia patients comprising: An acoustic sensor configured to be coupled to one of a nasal cannula or face mask of the anesthesia patient; A processer coupled to the acoustic sensor and configured to i) Detect patient speech and isolate and amplify the patient speech and ii) Detect at least one of a breathing rate of the patient or aspiration of the patient; and An audio visual display coupled to the processor and providing an audio and/or visual display of the isolated and amplified speech of the patient, and displaying results for at least one of a breathing rate of the patient or aspiration of the patient.

The acoustic sensor platform for anesthesia patients according to one embodiment of the invention can provide wherein the step of detecting patient speech and isolating and amplifying the patient speech includes providing real time dictation of the words of the patient to be displayed on the audio visual display. Additionally the invention may provide that the step of detecting patient speech and isolating and amplifying the patient speech includes noise cancellation to remove undesired background noise to isolate the patient's voice and amplify this patient voice signal for the operator which isolated and amplified audio signal is transmitted over the audio visual display. The acoustic sensor platform for anesthesia patients according to the invention may provide wherein an audible and dictated textual record of the isolated and amplified patient speech during a proceeding is automatically created and stored.

The acoustic sensor platform for anesthesia patients according to one aspect of the invention may provide wherein the platform detects a breathing rate of the patient, and wherein the detection of the breathing rate includes apneic detection of an apneic episode. The audio visual display may visually displays results of the breathing rate/apneic episode detection in real time and the audio visual display may alert the operator of dangerous or significant conditions of the patients breathing rate. A record of the detected breathing rate during a proceeding may be automatically created and stored.

The acoustic sensor platform for anesthesia patients according to one aspect of the invention may provide wherein the platform detects aspiration of the patient wherein the acoustic sensor picks up audible signals indicative of regurgitation/aspiration of the patient. The audio visual display may alert the operator of dangerous or significant conditions related to regurgitation/aspiration of the patient. A record of the detected patient aspiration during a proceeding may be automatically created and stored.

The acoustic sensor platform for anesthesia patients according to one aspect of the invention may further include additional physiologic sensors such as CO2 sensors, HCL sensors and temperature sensors on the platform and coupled to the processor to supplement the acoustic sensor.

One aspect of the present invention provides a method of Pain Mitigation, Apnea Detection, Aspiration Detection and Patient Communication in Anesthesia Patients comprising the steps of: Coupling an acoustic sensor to one of a nasal cannula or face mask of the anesthesia patient; Detecting patient speech and isolate and amplify the patient speech via a processer coupled to the acoustic sensor; Detecting at least one of a breathing rate of the patient or aspiration of the patient via a processer coupled to the acoustic sensor; providing an audio and/or visual display of the isolated and amplified speech of the patient on an audio visual display coupled to the processor; and displaying results for at least one of a breathing rate of the patient or aspiration of the patient on the audio visual display.

The features that characterize the present invention are pointed out with particularity in the claims which are part of this disclosure. These and other features of the invention, its operating advantages and the specific objects obtained by its use will be more fully understood from the following detailed description in connection with the attached figures.

DESCRIPTION OF THE PREFERRED EMBODIMENTS

Figure 1A:
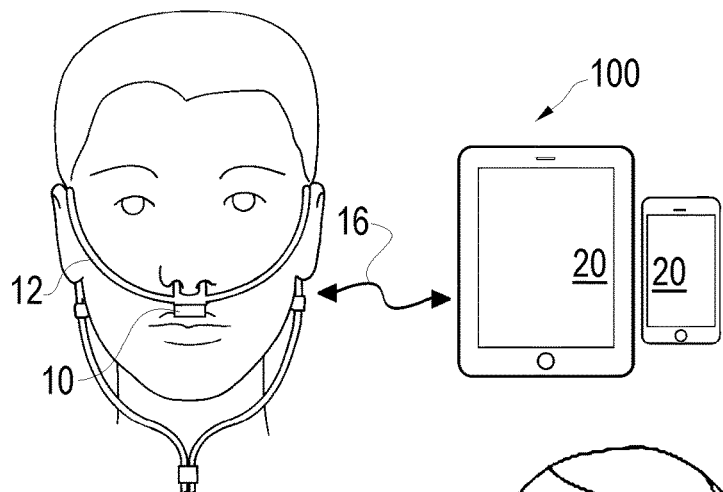
FIG. 1A is a schematic view of an acoustic sensor based apparatus for pain mitigation, apnea detection, aspiration detection and patient communication in anesthesia patients according to one embodiment of the present invention.

The present invention relates to an acoustic sensor platform based method and apparatus 100 for pain mitigation, apnea detection, aspiration detection and patient communication in anesthesia patients. FIG. 1A is a schematic view of an acoustic sensor based apparatus 100 according to one embodiment of the present invention in which the acoustic sensor 10 is coupled to a nasal cannula 12 of an anesthesia patient in a position adjacent the nasal passages of the patient. As described in FIG. 2, the acoustic sensor 10 forms a Bluetooth enabled patient communication platform and physiologic monitor platform for communication with, and selective physiologic parameter monitoring of, the patient. The sensor 10 is wirelessly connected 16, via Bluetooth or other wireless coupling, to a display device 20 of the operator (anesthesiologist).

The display 20 of the operator is a personal computer (PC) and generally a tablet or a smartphone. A tablet computer, commonly shortened to tablet, is a portable PC, typically with a mobile operating system and LCD touchscreen display processing circuitry, and a rechargeable battery in a single thin, flat package. Tablets, being computers, do what other PC do, but often lack some input/output (I/O) capabilities that others have. Modern tablets largely resemble modern smartphones, the only differences being that tablets are often larger than smartphones and may not support access to a cellular network. A smartphone is essentially a handheld PC with a mobile operating system and an integrated mobile broadband cellular network connection for voice, SMS, and Internet data communication; and essentially all smartphones also support Wi-Fi. A tablet and smartphone forming the device 20 have the necessary audio inputs/outputs to form the communications platform of the present invention and the video display for other aspects of the monitoring system of apparatus or platform 100.

The wireless connection 16 is used to describe a telecommunications protocol that uses electromagnetic waves, rather than a hard wire connection, for transmitting signals of interest. Bluetooth technology, represented schematically by the Bluetooth transmitter 22 in FIG. 2, is the preferred wireless method and defines an effective standard short-range protocol for coupling electronic devices.

Figure 1B:
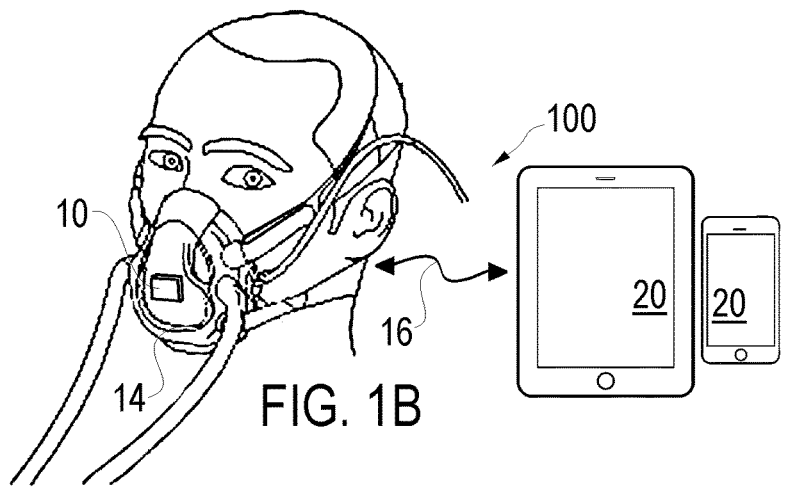
FIG. 1B is a schematic view of an acoustic sensor based apparatus for pain mitigation, apnea detection, aspiration detection and patient communication in anesthesia patients according to another embodiment of the present invention.

FIG. 1B is a schematic view of an acoustic sensor based apparatus 100 according to another embodiment of the present invention in which the acoustic sensor 10 is coupled to a mask 14 of an anesthesia patient in a position adjacent the vents of the mask 14 of the patient. The main difference between the embodiment of FIGS. 1A and 1B is that one is configured to couple the sensor 10 to a conventional nasal cannula while the other is constructed to couple the sensor to a mask 14. Outside of this difference the operation of the two embodiments will be substantially identical.

Figure 2:
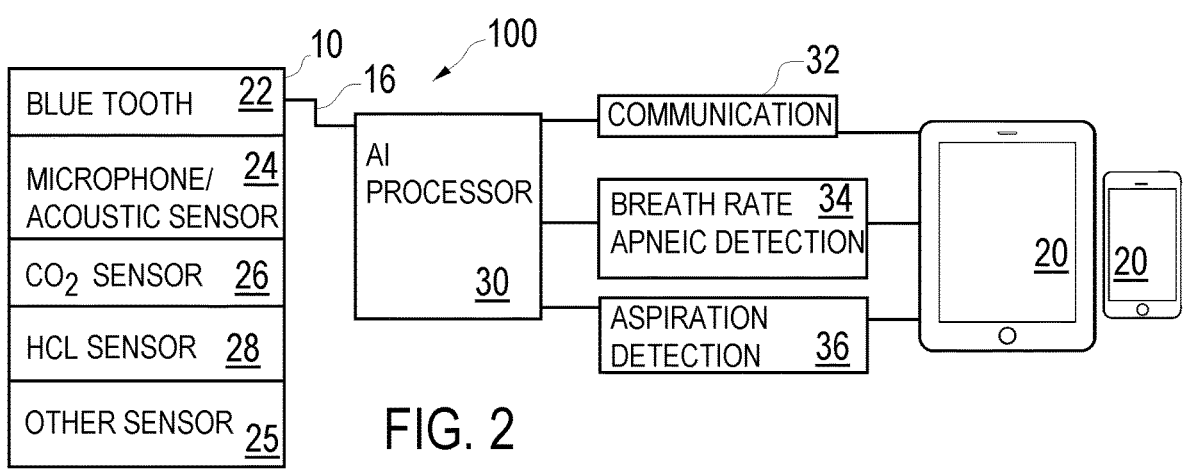
FIG. 2 is a schematic view of the acoustic sensor based apparatus of FIGS. 1A and B and associated signal processing.

FIG. 2 schematically outlines the associated signal processing for the acoustic sensor based apparatus 100 of FIGS. 1A and B. The sensor 10 includes Bluetooth technology, shown by transmitter/receiver 22, for forming the wireless coupling 16 with the processor 30 in the display 20. The processor 30 could be removed from the display 20 and housed in a separate device that is coupled to the display 20, even possibly be cloud based, but the display 20 is generally preferable as it avoids communication interruptions of lags.

The sensor 10 includes an acoustic sensor or microphone 24 for obtaining the audible inputs from the patient. A microphone 24 broadly is a transducer that converts sound into an electrical signal. Microphones are often categorized by the specific method used to convert the air pressure variations of a sound wave to an electrical signal. The most common microphone is a dynamic microphone, which uses a coil of wire suspended in a magnetic field; a condenser microphone, which uses the vibrating diaphragm as a capacitor plate, and the piezoelectric microphone, which uses a crystal of piezoelectric material. Any microphone type can be used as acoustic sensor 24 provided it is compact and is sufficient to pick up the patient's audible and physiologic signals.

In addition to the microphone or audible or acoustic sensor 24 the sensor 10 includes a $CO_2$ sensor 26 sufficient for capnography, namely the monitoring of the concentration or partial pressure of carbon dioxide ($CO_2$). See for example CO2 sensors from E+E Elektronik, SenseAir'sK30 10,000 ppm CO2 sensor, and the SprintIR6S 5% CO2 Sensor (which is capable of measuring CO2 levels up to 20 times per second).

The sensor 10 may optionally include a hydrochloric acid (HCL) sensor 28 for measuring HCL concentrations of select samples. HCl is the primary acid found in the stomach, and thus the HCL sensor 28 can be helpful for detecting regurgitation of the patient relevant for aspiration detection. Regarding acceptable HCL selection sensor, Detcon Model DM-700-HCL from 3M is a HCL sensor designed to detect and monitor Hydrogen Chloride in air over the range of 0-30 ppm using electrochemical sensor technology. Mil-ram technology, Inc.'s Tox-Array 2102 sensor detects HCL at 0.0 to 20.0 ppm along with other gasses. MSA's TS4000H sensor detects HCL at 0.0 to 20.0 ppm along with other gasses. Global Detection Systems Corp.'s GDS-49 sensor detects HCL at 0.0 to 30.0 ppm along with other gasses. Other sensor technology may be implemented for HCL detection such as photoplethysmography sensing technology utilized for HCL detection based upon HCL light absorption.

The sensor 10 can accommodate other physiologic parameter sensors 25 as desired, such as a temperature sensor, PH sensor or other desired sensor.

The signal processor 30 is preferably an artificial intelligence based or artificial neural network based signal processing system for processing the acoustic signals from sensor 24 in a patient operator communication platform 32, a breathing rate/apneic detection monitor 34, and a regurgitation/aspiration detection monitor 36 as discussed below. The artificial intelligence based or artificial neural network based signal processor 30 is intended to mean that the processor is expected to be adaptive and learn as it moves forward to improve the results. The specifics and operations of such systems are known in the art.

The communication platform 32 signal processing is effectively using the microphone 24 to pick up the speech or voice of the patient and isolate and amplify this signal so the operator can more easily hear and or receive the spoken words or speech sounds of the patient though the display device 20. The speech sounds of the patient are distinguished herein from the other physiologic sounds of the patient related to breathing and aspiration. The speech is likely to be mostly verbal, but grunting and other nonverbal vocal sounds are considered herein as speech.

One method of isolation and amplification is to provide real time dictation of the words of the patient to the audio visual display 20. The operator reading the spoken words on display 20 substantially simultaneously with hearing the patient can effectively "isolate and amplify" the voice signal sufficiently for the operator Preferably, the processing 30 also uses noise cancellation to remove undesired background noise to isolate the patient's voice and amplify this patient voice signal for the operator which isolated and amplified audio signal can be transmitted over the display 20.

In the medical fields, MRI sound systems and the associated signal processing form a basis for this aspect of the system or apparatus 100. Capturing the voice of the patient in the present environment is considered easier than in the much noisier MRI field, although the voice of the patient here may be more subtle due to the sedation level.

The microphone 24 and the communication platform (via 32) of the apparatus 100 allow the patient to more easily communicate with the anesthesiologist. Improved communication is believed to allow for substantial pain mitigation. Even if the audible patient speech sounds are non-verbal (e.g., grunts), this input to the anesthesiologist can improve the patient monitoring. The communication via the device 20 also allows an audible, and/or dictated textual record of the proceeding to be automatically created and stored. The invention provides that an audible, and/or dictated textual record of the isolated and amplified patient speech during a proceeding is automatically created and stored. The use of a dictated display and a simultaneous auditory display of patient sounds can further enhance communication. For example where the doctor was not exactly sure of what he heard over the speaker of device 20, the text display of the same patient comments can clarify this for the doctor. Alternatively is the dictation is slightly off, the hearing of the patient's own voice can assist the doctor in clarifying what was actually said by the patient. Thus the use of both an auditory output and a textual output are believed to improve communications by reinforcing, cross-checking and supplementing each other, The breathing rate/apneic episode detection 34 signal processing is effectively using the microphone 24 to pick up the audible signals indicative of breathing of the patient. The apneic detection is using this rate detector to determine when breathing rate is low or 0 for an apneic episode. Using audible sensor(s) for tracking breathing rates of a patient, alone, is known and is sometimes called respiratory acoustic monitoring. See *Performance of Masimo Rainbow Acoustic Monitoring for Tracking Changing Respiratory Rates Under Laryngeal Mask Airway General Anesthesia for Surgical Procedures in the Operating Room: A Prospective Observational Study*, Atkins, Joshua H. MD, PhD; Mandel, Jeff E. MD, MS *Anesthesia & Analgesia*: December 2014—Volume 119—Issue 6—p 1307-1314. See also the Masimo Pulse CO-Oximeter (Masimo Corporation, Irvine, Calif.) with acoustic monitoring technology that measures respiratory rate based on analysis of acoustic signals generated across the upper airway during turbulent flow with breathing and has been compared with capnography for accuracy. See also the Acoustic Sleep Apnea Detector developed by Vanderbilt University 2010 in which it was found that a tracheal breath sound has a characteristic frequency between 400 and 700 Hz and the collected sound waves were analyzed to detect a breath by comparing the frequency content of the wave with this frequency range.

It has been known that accurate monitoring of respiratory rate may be useful for the early detection of patient deterioration. Respiratory acoustic monitoring for respiratory rate monitoring has been demonstrated to provide accurate respiratory rates in patients recovering from anesthesia.

Where the CO2 monitor 26 is present this result can be combined with the audible inputs for calculating and displaying the breath rate/apneic episodes. It is envisioned that the display 20 can visually display the results of this breathing rate/apneic episode detection 34 signal processing in real time and visually and/or audibly alert the operator of dangerous or significant conditions. The display 20 allows for an easy record of the entire session to be maintained as well, specifically the display signals are recorded for a session whereby a record of the detected breathing rate and/or apneic episodes detected during a proceeding is automatically created and store.

The regurgitation/aspiration detection monitor 36 signal processing is effectively using the microphone 24 to pick up the audible signals indicative of regurgitation/aspiration of the patient. Predictive modeling may be implemented identifying for changes in respiration rate, pattern, etc as well as audible clues which would help to alert for depth of anesthesia and the patients ability to protect his/her airway e.g. passive reflux related to laxity in lower esophageal sphincter tone. Again the other sensors, namely the HCL sensor 28 can supplement this monitor result. The display 20 can visually display the results of this regurgitation/aspiration detection monitor 36 signal processing in real time and visually and/or audibly alert the operator of dangerous or significant conditions related to regurgitation/aspiration of the patient. The acoustic sensor platform for anesthesia patients according to the invention provides that a record of the detected patient aspiration during a proceeding is automatically created and stored. The display allows for an easy record of the entire session to be maintained as well.

While the invention has been shown in several particular embodiments it should be clear that various modifications may be made to the present invention without departing from the spirit and scope thereof. The scope of the present invention is defined by the appended claims and equivalents thereto.

What is claimed is:

1. An acoustic sensor platform for anesthesia patients comprising:
   a) An acoustic sensor configured to be coupled to one of a nasal cannula or face mask of an anesthesia patient;
   b) A processer coupled to the acoustic sensor and configured to
      i) Detect patient speech and isolate and amplify the patient speech;
      ii) Detect at least one of a breathing rate of the patient or aspiration of the patient;
   c) An audio visual display coupled to the processor and providing an audio and/or visual display of the isolated and amplified speech of the patient, and displaying results for at least one of the breathing rate of the patient or the aspiration of the patient.

2. The acoustic sensor platform for anesthesia patients according to claim 1 wherein the detecting patient speech and isolating and amplifying the patient speech includes providing real time dictation of the words of the patient to be displayed on the audio visual display.

3. The acoustic sensor platform for anesthesia patients according to claim 2 wherein detecting patient speech and isolating and amplifying the patient speech includes noise cancellation to remove undesired background noise to isolate a voice signal of the patient and amplify this patient voice signal for an operator which isolated and amplified patient voice signal is transmitted over the audio visual display.

4. The acoustic sensor platform for anesthesia patients according to claim 3 wherein an audible and dictated textual record of the isolated and amplified patient speech during a proceeding is automatically created and stored.

5. The acoustic sensor platform for anesthesia patients according to claim 1 wherein the detecting patient speech and isolating and amplifying the patient speech includes noise cancellation to remove undesired background noise to isolate a voice signal of the patient and amplify this patient voice signal for an operator which isolated and amplified patient voice signal is transmitted over the audio visual display.

6. The acoustic sensor platform for anesthesia patients according to claim 1 wherein an audible and/or dictated textual record of the isolated and amplified patient speech during a proceeding is automatically created and stored.

7. The acoustic sensor platform for anesthesia patients according to claim 1 wherein the platform detects the breathing rate of the patient.

8. The acoustic sensor platform for anesthesia patients according to claim 7 wherein the detection of the breathing rate includes apneic detection of an apneic episode.

9. The acoustic sensor platform for anesthesia patients according to claim 8 wherein the audio visual display visually displays results of the breathing rate/apneic episode detection in real time.

10. The acoustic sensor platform for anesthesia patients according to claim 9 wherein the audio visual display alerts an operator of dangerous or significant conditions of the patients breathing rate.

11. The acoustic sensor platform for anesthesia patients according to claim 9 wherein a record of the detected breathing rate during a proceeding is automatically created and stored.

12. The acoustic sensor platform for anesthesia patients according to claim 1 wherein the platform detects the aspiration of the patient wherein the acoustic sensor picks up audible signals indicative of regurgitation/aspiration of the patient.

13. The acoustic sensor platform for anesthesia patients according to claim 12 wherein the audio visual display alerts an operator of dangerous or significant conditions related to regurgitation/aspiration of the patient.

14. The acoustic sensor platform for anesthesia patients according to claim 12 wherein a record of the detected patient aspiration during a proceeding is automatically created and stored.

15. The acoustic sensor platform for anesthesia patients according to claim 12 wherein the platform also detects the breathing rate of the patient and wherein the detection of the breathing rate includes apneic detection of an apneic episode.

16. The acoustic sensor platform for anesthesia patients according to claim 15 wherein the audio visual display alerts the operator of dangerous or significant conditions related to the breathing rate and the regurgitation/aspiration of the patient.

17. The acoustic sensor platform for anesthesia patients according to claim 12 wherein a record of the detected breathing rate and the patient aspiration during a proceeding is automatically created and stored.

18. The acoustic sensor platform for anesthesia patients according to claim 1 further including additional physiologic sensors on the platform and coupled to the processor.

19. A method of Pain Mitigation, Apnea Detection, Aspiration Detection and Patient Communication in Anesthesia Patients comprising the steps of:
  a) Coupling an acoustic sensor to one of a nasal cannula or face mask of an anesthesia patient;
  b) Detecting patient speech and isolate and amplify the patient speech via a processer coupled to the acoustic sensor;
  c) Detecting at least one of a breathing rate of the patient or aspiration of the patient via a processer coupled to the acoustic sensor;
  d) providing an audio and/or visual display of the isolated and amplified speech of the patient on an audio visual display coupled to the processor; and
  e) displaying results for at least one of the breathing rate of the patient or the aspiration of the patient on the audio visual display.

\* \* \* \* \*